United States Patent
Magno et al.

(10) Patent No.: US 12,336,731 B2
(45) Date of Patent: Jun. 24, 2025

(54) HIGH SPEED BURR WITH FLEX SHAFT COOLING AND IMPROVED SUCTION

(71) Applicant: GYRUS ACMI, INC., Westborough, MA (US)

(72) Inventors: Joey Magno, Dudley, MA (US); Jake Terravecchia, Brighton, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 348 days.

(21) Appl. No.: 18/045,205

(22) Filed: Oct. 10, 2022

(65) Prior Publication Data
US 2023/0131647 A1    Apr. 27, 2023

Related U.S. Application Data

(60) Provisional application No. 63/266,949, filed on Jan. 20, 2022, provisional application No. 63/270,880, filed on Oct. 22, 2021.

(51) Int. Cl.
A61B 17/32    (2006.01)
A61B 17/24    (2006.01)

(52) U.S. Cl.
CPC ........ *A61B 17/32002* (2013.01); *A61B 17/24* (2013.01); *A61B 2017/320004* (2013.01); *A61B 2017/320032* (2013.01); *A61B 2217/007* (2013.01)

(58) Field of Classification Search
CPC .............. A61B 17/24; A61B 17/32002; A61B 2017/320004; A61B 2017/320032; A61B 2217/007
See application file for complete search history.

(56) References Cited

U.S. PATENT DOCUMENTS

| | | | | |
|---|---|---|---|---|
| 3,732,858 A | * | 5/1973 | Banko | A61B 17/32002 606/107 |
| 4,955,882 A | * | 9/1990 | Hakky | A61B 18/24 606/14 |
| 5,437,630 A | * | 8/1995 | Daniel | A61B 17/32002 606/180 |
| 5,685,838 A | * | 11/1997 | Peters | A61B 17/32002 606/171 |
| 5,792,167 A | * | 8/1998 | Kablik | A61M 3/0201 606/180 |
| 6,068,641 A | * | 5/2000 | Varsseveld | A61B 17/32002 606/170 |

(Continued)

*Primary Examiner* — Alexander J Orkin
(74) *Attorney, Agent, or Firm* — Schwegman Lundberg & Woessner, P.A.

(57) ABSTRACT

A disposable attachment of the handheld surgical instrument having a distal section extending from the handpiece is provided. The disposable attachment has a proximal tube extending from the disposable attachment. The distal section includes an outer tube and a flexible shaft disposed within the outer tube. The flexible shaft couples with the proximal tube via a proximal coupler at a proximal end of the flexible shaft. The distal section also has an irrigation hypotube, a cooling orifice, and a cutting implement. The irrigation hypotube is disposed on an outer surface of the outer tube and the cooling orifice is disposed at a distal end of the distal section. The cutting implement is disposed at a distal end of the distal section opposite the handpiece.

20 Claims, 10 Drawing Sheets

(56) References Cited

U.S. PATENT DOCUMENTS

| | | | |
|---|---|---|---|
| 6,132,448 A * | 10/2000 | Perez | A46B 5/0087 606/180 |
| 10,413,305 B2 | 9/2019 | Magno et al. | |
| 2005/0054972 A1 * | 3/2005 | Adams | A61B 17/24 606/180 |
| 2007/0100336 A1 * | 5/2007 | McFarlin | A61B 18/14 606/45 |
| 2009/0270791 A1 * | 10/2009 | Todd | A61M 13/003 604/164.03 |
| 2011/0313286 A1 * | 12/2011 | Whayne | A61B 18/148 600/431 |
| 2014/0276949 A1 * | 9/2014 | Staunton | A61B 17/32002 606/130 |
| 2015/0245851 A1 * | 9/2015 | McGuckin, Jr. | A61B 17/32002 606/159 |
| 2018/0070981 A1 * | 3/2018 | Govari | A61B 17/24 |
| 2018/0271544 A1 * | 9/2018 | Magno | A61B 17/1644 |
| 2018/0317952 A1 * | 11/2018 | Jamous | A61M 25/0082 |
| 2019/0231379 A1 * | 8/2019 | Edwards | A61M 1/77 |
| 2019/0247068 A1 * | 8/2019 | Whipple | A61B 17/3205 |
| 2021/0100564 A1 | 4/2021 | Magno et al. | |
| 2021/0100571 A1 * | 4/2021 | Ly | A61B 17/320016 |

\* cited by examiner

HIGH SPEED BURR WITH FLEX SHAFT COOLING AND IMPROVED SUCTION

PRIORITY CLAIM

This application claims the benefit of priority to U.S. Provisional Patent Application Ser. No. 63/270,880, filed Oct. 22, 2021, and U.S. Provisional Patent Application Ser. No. 63/266,949, filed Jan. 20, 2022, the contents of which are hereby incorporated by reference in their entireties.

TECHNICAL FIELD

This document pertains generally, but not by way of limitation, to surgical devices that can be used for various surgical procedures. More specifically, but not by way of limitation, the present application relates to a handheld surgical instrument.

BACKGROUND

Occlusions within cavities of patients, such as sinus cavities, can cause a number of issues with a patient. These issues can include, for example, chronic rhinosinusitis, a deviated septum, nasal polyps, or the like. In order to remove these or other types of occlusions within cavities, a physician can use a handheld surgical instrument having a microdebrider or a drill. Microdebriders can be used with a variety of implements depending on the procedure being performed. A microdebrider can include a cutting implement that can rotate at high speeds, such as a burr, a dremel, or a drill. The microdebrider can be used in Rhinologic procedures to remove softer tissues of the sinuses and in Otologic procedures to remove bone in, and around, the ear. For example, a pre-bent implement having cutting implements can be used when surgery is being performed at difficult to reach surgical sites, such as the aforementioned sinus cavities.

In order to facilitate removal of tissue and bone at a surgical site, the implement rotates at high speeds, where the high speeds in combination with a surface of the implement function to remove tissue and bone from the surgical site. During operation, an issue that can arise with an implement rotating at high speeds is heat that is generated within the handheld surgical instrument. Moreover, another issue that can arise with an implement rotating at high speeds is friction between an assembly that couples the implement with the handheld surgical instrument. The friction created between the assembly that couples the implement with the handheld surgical instrument can further increase the heat created during operation of the handheld surgical instrument. During operation, the implement itself may reach temperatures during use that may burn tissue and bone at a surgical site. In addition, the heat generated during rotation of the implement can lead to premature failure of the handheld surgical instrument during a surgical procedure.

Accordingly, what is needed is a handheld surgical instrument that includes an assembly that facilitates cooling of the handheld surgical instrument during operation.

SUMMARY

Examples of the present disclosure relate to cooling a disposable attachment of a surgical instrument during operation of the handheld surgical instrument. The handheld surgical instrument can include a handpiece along with a distal section extending from the handpiece. The disposable attachment can include a proximal tube that extends from a housing of the handpiece to the distal section. The distal section can include an outer tube with a flexible shaft disposed within the outer tube. The outer tube can have an inner diameter that can be greater than an outer diameter of the flexible shaft. Thus, in an example, when the flexible shaft is within the outer tube, a port can be formed between the flexible shaft outer diameter and the outer tube inner diameter. In addition, a cutting implement can be disposed at a distal end of the outer tube. The distal section can also include an irrigation hypotube on an outer surface of the outer tube that extends from the handpiece to a distal end of the distal section.

In an example, the irrigation hypotube can include a cooling orifice disposed near the distal end of the of the distal section. The irrigation hypotube can be configured to deliver irrigant to the cutting implement and the flexible shaft. In particular, the cooling orifice can provide irrigant to the port defined between the flexible shaft and the outer tube during operation of the handheld surgical instrument. The irrigation hypotube can also include an outlet that is adjacent the cutting implement. The irrigation hypotube can deliver irrigant to the cutting implement via the irrigation hypotube outlet that is adjacent the cutting implement. As such, the irrigation hypotube can simultaneously deliver first irrigant to the cutting implement and deliver second irrigant to the outer tube and the flexible shaft via the irrigation hypotube outlet and the cooling orifice. In examples, the cooling orifice is located upstream of the irrigation hypotube outlet at the irrigation hypotube such that the irrigation hypotube outlet and the cooling orifice share irrigant delivered via the irrigation hypotube.

In an example, the proximal tube extending from the handpiece can couple with the flexible shaft via a proximal coupling. In this example, the handheld surgical instrument includes a bushing disposed about the proximal tube where an area between the proximal coupling and the bushing about the proximal tube can define an irrigant outlet chamber. The proximal tube can have an orifice disposed within the irrigant outlet chamber. The proximal coupling can be configured to pull the irrigant from within the gap between the outer tube and the flexible shaft to the irrigant outlet chamber. In an example, the proximal coupling can have a threaded configuration. During operation of the handheld surgical instrument, the proximal coupling can rotate along with the flexible shaft and the proximal tube. The helical configuration of the proximal coupling allows the proximal coupling to function as a screw compressor, thereby creating vacuum pressure. The vacuum pressure can pull the irrigant from the port in the outer tube towards the irrigant outlet chamber, where the irrigant can flow into the proximal tube orifice and out of the handheld surgical instrument.

In an example, the outer tube and the flexible shaft are configured to bend such that a surgeon may extend the distal end of the handheld surgical instrument into a patient during a surgical procedure. Thus, during operation, when the outer tube and the flexible shaft are bent, irrigant passes in the port defined between the flexible shaft and the outer tube, thereby minimizing heat that can be created from friction that occurs between the flexible shaft and the outer tube in the bent configuration during operation of the handheld surgical instrument.

An advantage includes the ability to minimize overheating of a disposable attachment of a surgical instrument while the disposable attachment operates at high rpms.

Another advantage includes providing cooling capabilities to a bendable disposable attachment of a surgical instrument while the disposable attachment operates at high rpms.

Another advantage relates to the ability to simultaneously use irrigant to enhance cooling of a disposable attachment of a surgical instrument during operation of the disposable attachment while at the same time using the irrigant to assist with the evacuation of debris from a surgical site.

DETAILED DESCRIPTION

Examples of the present disclosure relate to cooling a handheld surgical instrument during operation of the handheld surgical instrument. The handheld surgical instrument can include a handpiece along with a distal section extending from the handpiece. The handpiece can include a proximal tube that extends from a housing of the handpiece to the distal section. The distal section can include an outer tube with a flexible shaft disposed within the outer tube. The outer tube can have an inner diameter that can be greater than an outer diameter of the flexible shaft. Thus, in an example, when the flexible shaft is within the outer tube, a port can be formed between the flexible shaft outer diameter and the outer tube inner diameter. In addition, a cutting implement can be disposed at a distal end of the outer tube. The distal section can also include an irrigation hypotube on an outer surface of the outer tube that extends from the handpiece to a distal end of the distal section. As will be discussed in further detail below, the handheld surgical instrument can include a cooling orifice along with distal and proximal couplers that can facilitate cooling of the handheld surgical instrument during operation.

Figure 1:
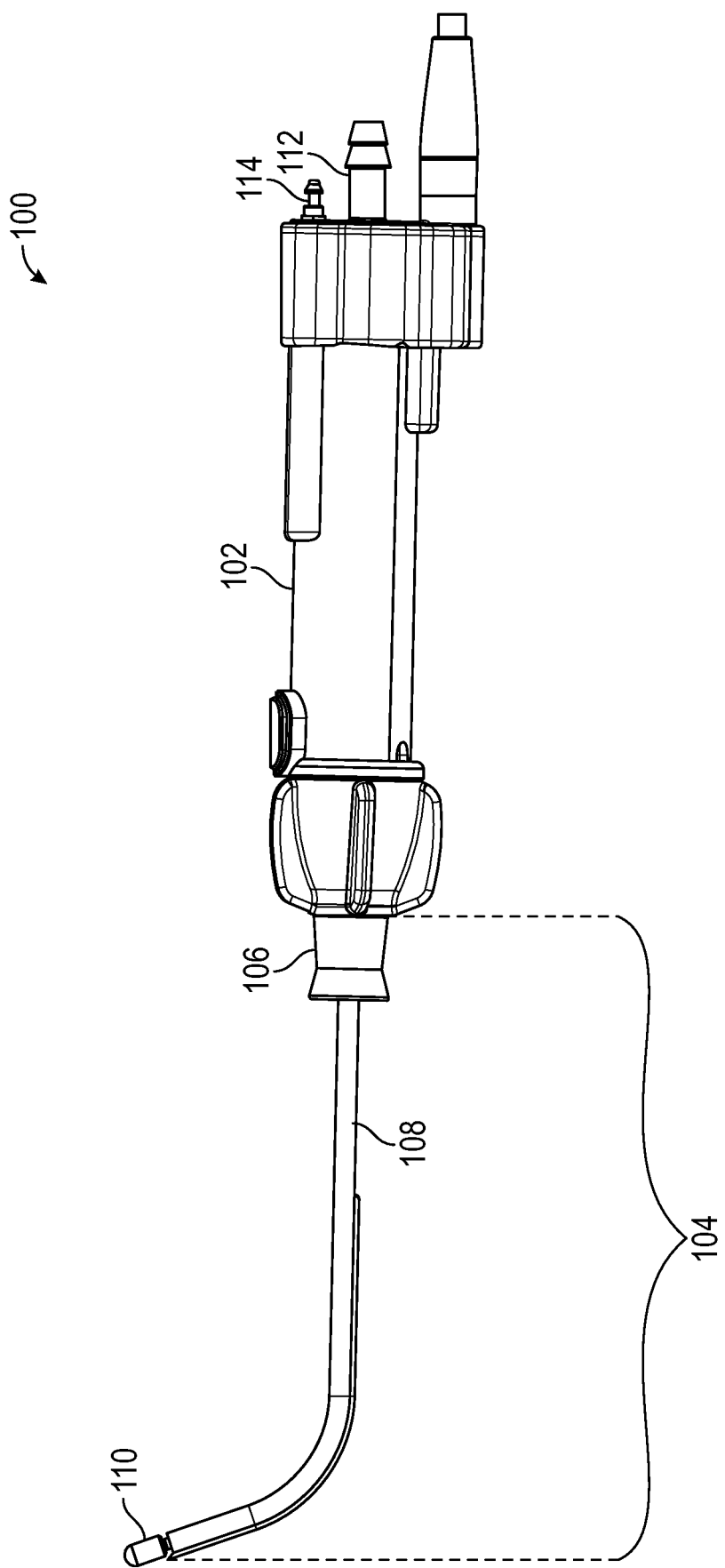
FIG. 1 illustrates a handheld surgical instrument, in accordance with at least one example of the present disclosure.

Now making reference to the Figures and more specifically FIG. 1, a handheld surgical device 100 is shown in accordance with at least one example of the present disclosure. The handheld surgical device 100 can include a handpiece 102 and a distal section 104 that can include an irrigation hub interface 106. In an example, the distal section 104 can extend from the handpiece 102 at the irrigation hub interface 106 where the irrigation hub interface 106 is part of the distal section 104. The distal section 104 can include an outer tube 108 that extends between the irrigation hub interface 106 and a cutting implement 110 disposed at a distal end of the outer tube 108. The cutting implement 110 can be any type of cutting implement, such as a burr tip, a burr tree tip, a double-cut rotary burr bit, a ball shaped burr, a dremel, a drill, or the like.

Figure 2:
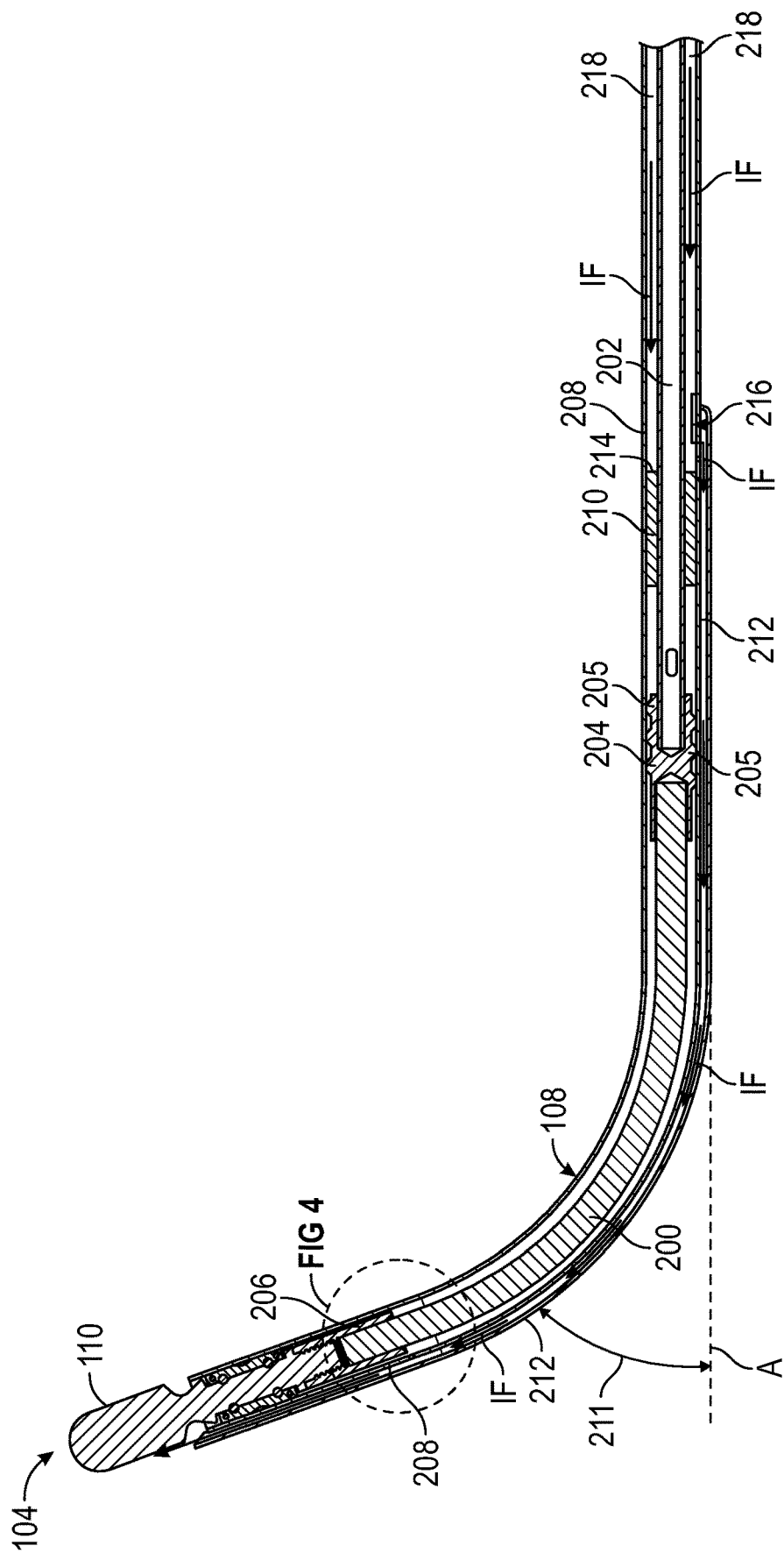
FIG. 2 shows an outer tube of the handheld surgical instrument of FIG. 1, in accordance with at least one example of the present disclosure.

In an example, the outer tube 108 can be a burr outer tube and house a flexible shaft 200, as shown with reference to FIG. 2. Now making reference to FIG. 2, an example of the outer tube 108 shown with reference to FIG. 1 is illustrated in accordance with at least one example of the present disclosure. In an example, the flexible shaft 200 can be disposed within the outer tube 108 and couple with a proximal tube 202 extending from the handpiece 102. In an example, the flexible shaft 200 can couple with the proximal tube 202 via a proximal coupler 204 also disposed within the outer tube 108. In an example, the proximal coupler 204 can include helicoils 205 disposed thereabout. Moreover, the flexible shaft 200 can extend within the outer tube 108 from the proximal coupler 204 to a distal coupler 206 and a cooling orifice 208. The distal coupler 206 and the cooling orifice 208 can be distally located relative to the proximal coupler 204 and the proximal tube 202 where the flexible shaft 200 can extend between the proximal coupler 204 and the distal coupler 206. In an example, the distal coupler 206 can couple the flexible shaft-shaft 200 with the cutting implement 110. Additionally, the distal section 104 can include a bushing 210 disposed about the proximal tube 202 within the outer tube 108. In an example, the bushing can be formed from polytetrafluoroethylene. As will be discussed further on, the bushing 210 can function to regulate irrigant flow within the outer tube 108.

Figure 9:
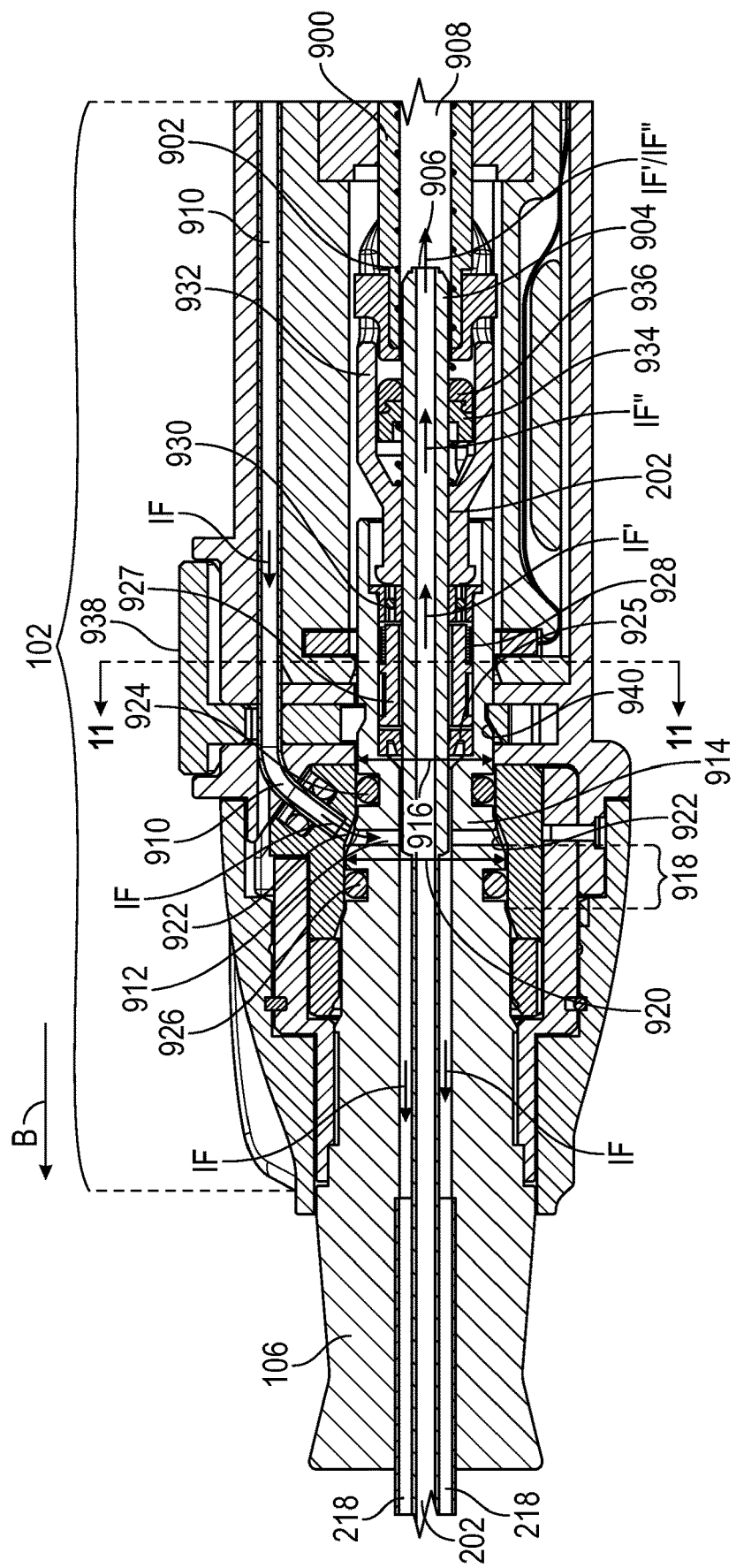
FIG. 9 is a schematic view of the handpiece and the irrigation hub of FIG. 1 in accordance with at least one example of the present disclosure.

In an example, the flexible shaft 200 can rotate within the outer tube 108 during operation of the handheld surgical device 100. In particular, the proximal tube 202 can operatively couple with a motor 900 (FIG. 9) of the handheld surgical device 100 such that during operation of the handheld surgical device 100, the motor 900 rotates the proximal tube 202. Moreover, as the proximal tube 202 rotates, by virtue of being secured with the proximal coupler 204, the proximal coupler 204 can also rotate with the proximal tube 202. In an example, as the proximal coupler 204 rotates, since the flexible shaft 200 can be secured with the proximal coupler 204, the flexible shaft 200 can also rotate with the proximal coupler 204. As the flexible shaft 200 rotates, the distal coupler 206 can also rotate with the flexible shaft 200 since the flexible shaft 200 is secured to the distal coupler 206. When the distal coupler 206 rotates, the cutting implement 110 can also rotate by virtue of the cutting implement 110 being secured to the distal coupler 206.

An issue that can arise during operation of the handheld surgical device 100 is friction that can occur between the flexible shaft 200 and the outer tube 108. Specifically, the flexible shaft 200 can include an outer diameter 300 that can be less than an inner diameter 302 of the outer tube 108, as shown with reference to FIG. 3. Thus, due to the difference between the outer diameter 300 and the inner diameter 302, the flexible shaft 200 can rotate within the outer tube 108 during operation of the handheld surgical device 100. Furthermore, as may be seen with reference to FIG. 2, the flexible shaft 200 can be capable of bending within the outer tube 108. In some examples, the flexible shaft 200 can be a stainless steel cable having a solid core with multiple coils disposed around the solid core. In some examples, the solid core in combination with the multiple coils allows for bending of the flexible shaft 200. In examples, the outer tube 108, along with the flexible shaft 200, can bend at an angle 211 between 15° and 90° relative to A in FIG. 2, preferably between 30° and 60° relative to A in FIG. 2, and more preferably at about 45° relative to A in FIG. 2.

However, during operation of the handheld surgical device 100, an outer surface 304 of the flexible shaft 200 can contact an inner surface 306 of the outer tube 108 by virtue of the bent configuration of the outer tube 108 and the flexible shaft 200. Contact between the flexible shaft outer surface 304 and the outer tube inner surface 306 can create friction which can create heat. In an example, in order to regulate heat generation that can occur during operation of the handheld surgical device 100, irrigant IF can be provided to the outer tube 108.

More specifically, the distal section 104 can include an irrigation hypotube 212 disposed on an outer surface of the outer tube 108. As may be seen with reference to FIG. 2, the irrigation hypotube 212 can extend from a proximal end 214 of the bushing 210 to the cutting implement 110. In an example, the outer tube 108 can include an irrigation port 216 in fluid communication with irrigant pathways 218 disposed between the outer tube 108 and the proximal tube 202. In an example, the irrigant IF flows from the handpiece 102 into and through the irrigant pathways 218 to the irrigation port 216. As noted above, in an example, the bushing 210 can regulate irrigant flow. In an example, the bushing proximal end 214 forces irrigant into the irrigation port 216, thereby regulating irrigant flow into the distal section 104. From the irrigation port 216, the irrigant IF flows into the irrigation hypotube 212 and towards both the cutting implement 110 and the cooling orifice 208.

Figure 4:
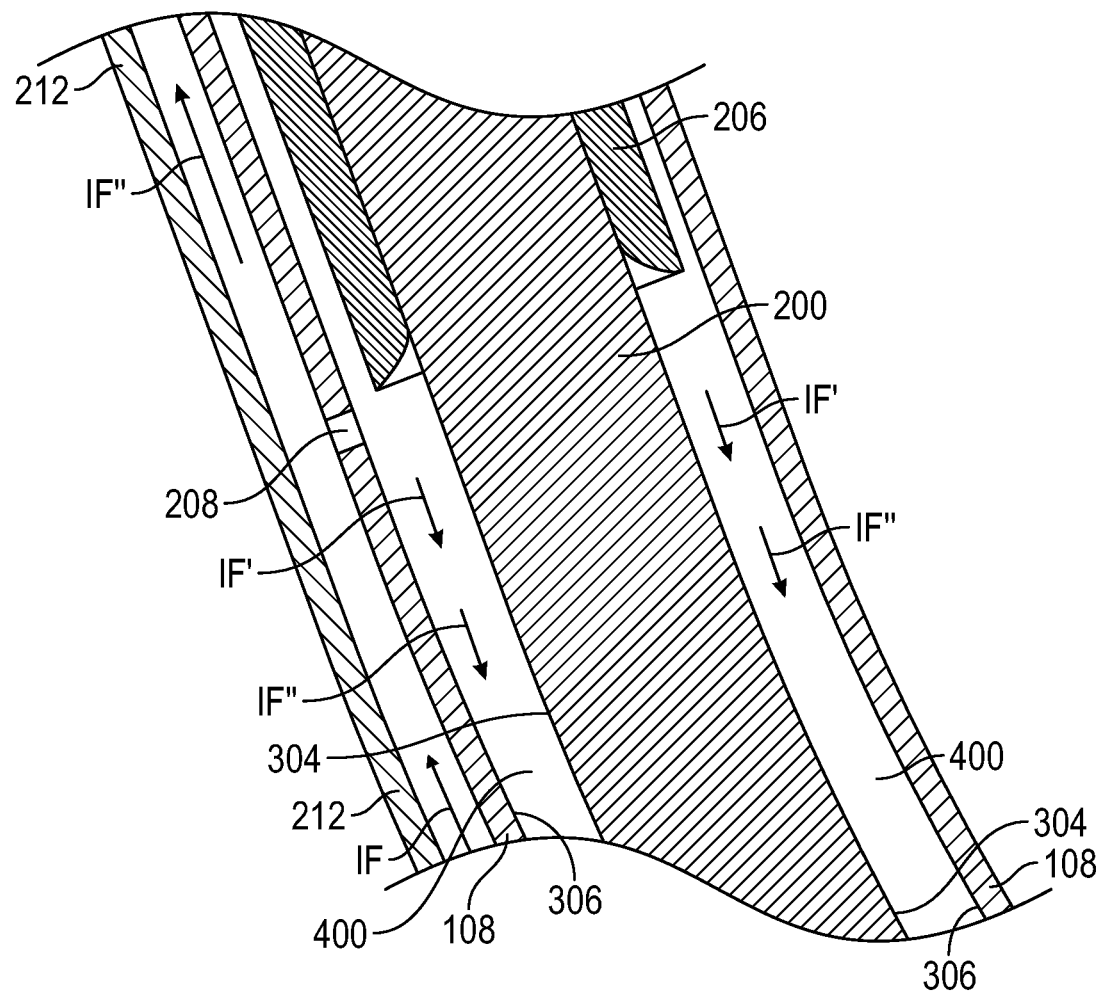
FIG. 4 illustrates a distal coupler disposed within the outer tube of the handheld surgical instrument of FIG. 1 along with irrigant flow at a distal end of the outer tube, in accordance with at least one example of the present disclosure.

Now making reference to FIG. 4, as the irrigant IF flows to the distal end of the outer tube 108, a portion IF' of the irrigant flows into the cooling orifice 208 and into ports 400 formed between the outer tube 108 and the flexible shaft 200. In this example, the irrigant portion IF' functions to cool the flexible shaft 200 during operation of the handheld surgical device 100. As noted above, during operation, friction between the flexible shaft outer surface 304 and the outer tube inner surface 306 creates heat. In an example, the irrigant portion IF' functions to remove heat created by the friction between the flexible shaft outer surface 304 and the outer tube inner surface 306. Moreover, the irrigant portion IF' flows through the ports 400 from the distal end of the outer tube 108 towards the proximal coupler 204. In particular, the difference between the outer diameter 300 and the inner diameter 302 creates a gap 309 through which the irrigant portion IF' can flow during heat removal.

Figure 5:
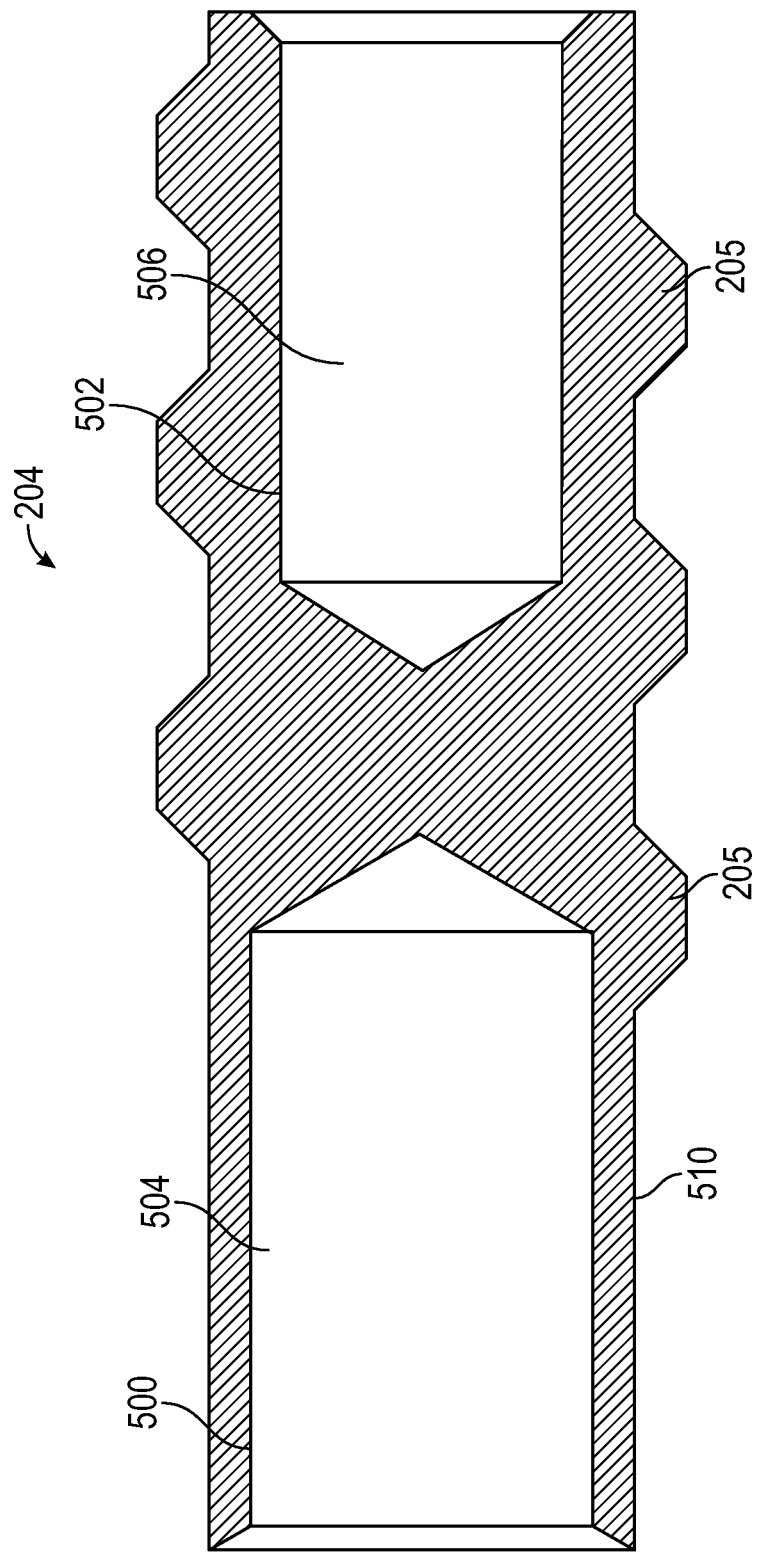
FIG. 5 illustrates a proximal coupler of FIG. 1, in accordance with at least one example of the present disclosure.
Figure 6A:
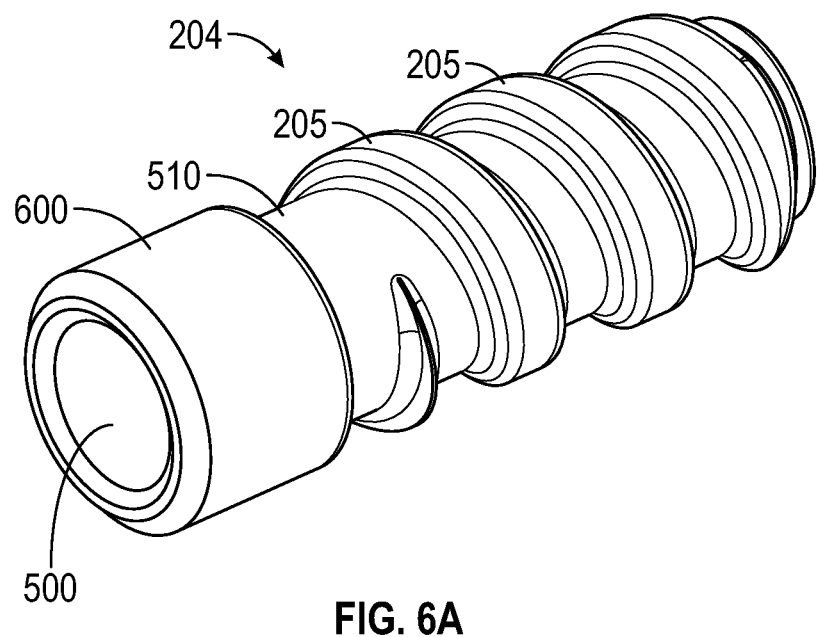
FIGS. 6A and 6B are alternative views of the proximal coupler of FIG. 5, in accordance with at least one example of the present disclosure.
Figure 6B:
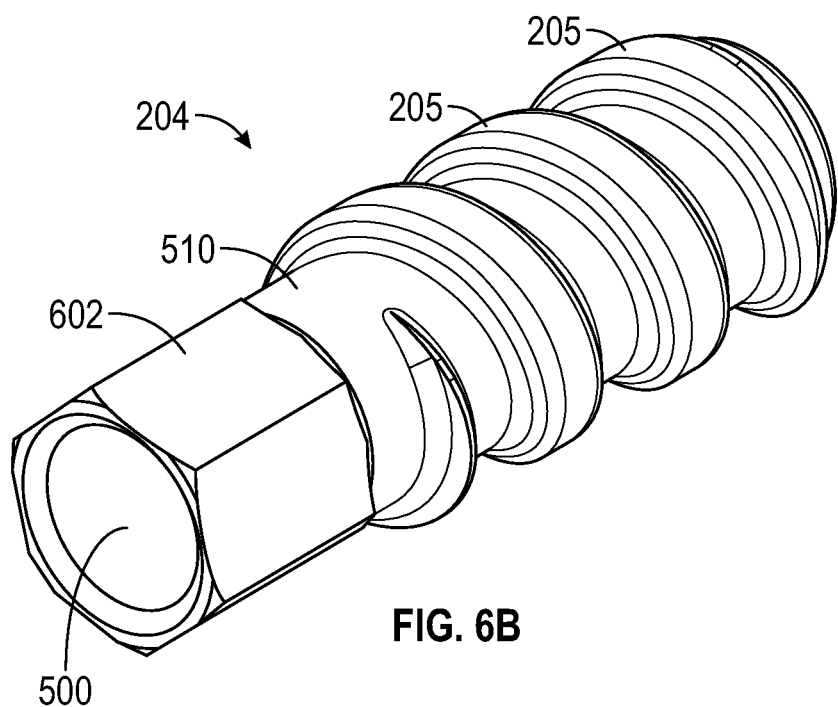

As noted above, the flexible shaft 200 can couple with the proximal tube 202 extending from the handpiece 102 via the proximal coupler 204. Now making reference to FIG. 5, the proximal coupler 204 can include a first proximal coupler cavity 500 and a second proximal coupler cavity 502 disposed opposite the first proximal coupler cavity 500. In an example, the first proximal coupler cavity 500 can be configured to receive a flexible shaft proximal end 504. In an example, the flexible shaft proximal end 504 can be crimped within the first proximal coupler cavity 500, where an outer surface 600 (FIG. 6A) of the proximal coupler 204 can be crimped to form a crimped surface 602 around the flexible shaft proximal end 504 (FIG. 6B). In addition to crimping, the flexible shaft proximal end 504 can be secured within the first proximal coupler cavity 500 via a frictional fit, soldering, an adhesive, or any other securing method. The second proximal coupler cavity 502 can be configured to receive a distal end 506 of the proximal tube 202. The distal proximal tube end 506 can be secured within the second proximal coupler cavity 502 via crimping, a frictional fit, soldering, an adhesive, or any other securing method. In addition to the first and second proximal coupler cavities 500 and 502, the proximal coupler 204 includes the helicoils 205 disposed on an outer surface 510 of the proximal coupler 204. As may be seen with reference to FIGS. 6A and 6B, the helicoils 205 form a threaded configuration on the proximal coupler outer surface 510.

Returning attention to FIG. 3, as noted above, the irrigant portion IF' can flow from the cooling orifice 218, around the flexible shaft 200 via the ports 400, and towards the proximal coupler 204. In an example, due to having the threaded configuration via the helicoils 205, the proximal coupler 204 can function as a screw compressor, thereby creating vacuum pressure. In an example, the vacuum pressure created by the rotation of the proximal coupler 204 and the helicoils 205 functions to pull the irrigant portion IF' from the cooling orifice 218 towards the proximal coupler 204.

In an example, when the irrigant portion IF' arrives at the proximal coupler 204, the irrigant portion IF' can flow between the helicoils 205 as shown by directional arrows A. Furthermore, the irrigant portion IF' can travel over the helicoils 205, as shown with regards to FIG. 3. In an example, the irrigant portion IF' can travel past the proximal coupler 204 as discussed above and into an irrigation outlet chamber 308 defined by the proximal coupler 204 and the bushing 210. In an example, the irrigation outlet chamber 308 can be defined by a proximal side 310 of the proximal coupler 204 and a distal side 312 of the bushing. Thus, the irrigation outlet chamber 308 can extend between the proximal coupler proximal side 310 and the bushing distal side 310. Moreover, a portion of the proximal tube 202 can be disposed within the irrigation outlet chamber 308.

In an example, the proximal tube 202 can include orifices 314 and 316. As may be seen with reference to FIG. 3, the proximal tube orifices 314 and 316 can be disposed within the irrigation outlet chamber 308. The orifice 314 can be disposed on a first side of the proximal tube 202 and the orifice 316 can be disposed on a second side of the proximal tube 202 opposite the orifice 314. Furthermore, as may be seen with reference to FIG. 3, the orifices 314 and 316 can be staggered with respect to each other. In an example, a suction can be applied to the orifices 314 and 316 such that the irrigant portion IF' can be pulled from the proximal coupler 204 and into the orifices 314 and 316 for evacuation from the handheld surgical device 100. Moreover, as mentioned above, the bushing 210 can function to regulate irrigant flow within the handheld surgical device 100. Via the bushing distal side 312, the bushing 310 can function, in conjunction with the orifices 314 and 316 and the vacuums provided at the orifices 314 and 316, to control the flow of irrigant out of the distal section 104.

Figure 7:
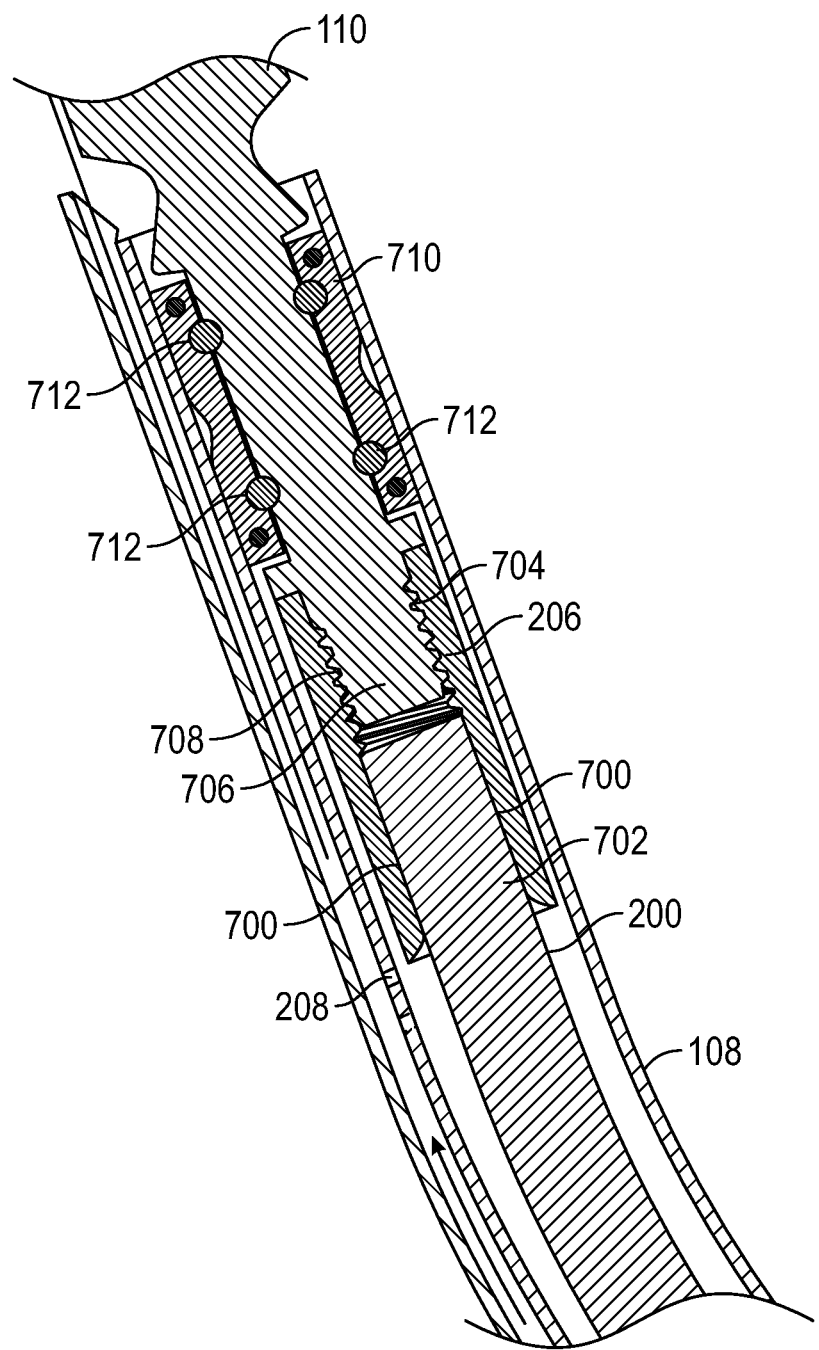
FIGS. 7 and 8 are alternative views of the distal coupler of FIG. 4, in accordance with at least one example of the present disclosure.

As noted above, the flexible shaft 200 can couple with the distal coupler 206 at a distal end of the handheld surgical device 100. The distal coupler 206 can couple the flexible shaft 200 with the cutting implement 110. In order to facilitate coupling, the distal coupler 206 can include a first cavity 700, which can be configured to receive a distal end 702 of the flexible shaft 200, as shown with reference to FIG. 7. The flexible shaft distal end 702 can be secured within the first distal coupler cavity 700 via crimping, a frictional fit, soldering, an adhesive, or any other securing method. Furthermore, the distal coupler 206 can include a second distal coupler cavity 704 opposite the first distal coupler cavity 700 as shown with reference to FIG. 7. The second distal coupler cavity 704 can be configured to receive a proximal end 706 of the cutting implement 110. In an example, the cutting implement proximal end 706 can be threaded where the second distal coupler cavity 704 includes threads 708 that are complementary to threads of the cutting implement proximal end 706. Thus, the cutting implement proximal end 706 can threadingly engage with the second distal coupler cavity 704 such that the cutting implement proximal end 706 can be secured within the second distal coupler cavity 704. It should be noted that while threads are shown and described as a method of securing the cutting implement proximal end 706 with the second distal coupler cavity 704, other methods can also be used, such as a frictional fit, soldering, an adhesive, or any other securing method.

In addition to being secured to the distal coupler 206, the cutting implement 110 can also be disposed within a bearing 710 having bearing ball grooves 712 that are formed in the bearing 710. In an example, the bearing 710 allows for rotation of the cutting implement 110 within the outer tube 108 during operation of the handheld surgical instrument 100. For a further discussion of the bearing 710, reference is made to U.S. application Ser. No. 17/031,389, the disclosure of which is hereby incorporated by reference in its entirety.

Returning attention to FIG. 4, as noted above, the irrigant portion IF' flows into the cooling orifice 208. In an example, while the irrigant portion IF' flows into the cooling orifice 208, an irrigant portion IF" does not flow into the cooling orifice 208 and instead flows towards the cutting implement 110. Thus, in an example, the irrigation hypotube 212 can simultaneously provide irrigant to the cooling orifice 208 and the cutting implement 110.

Figure 8:
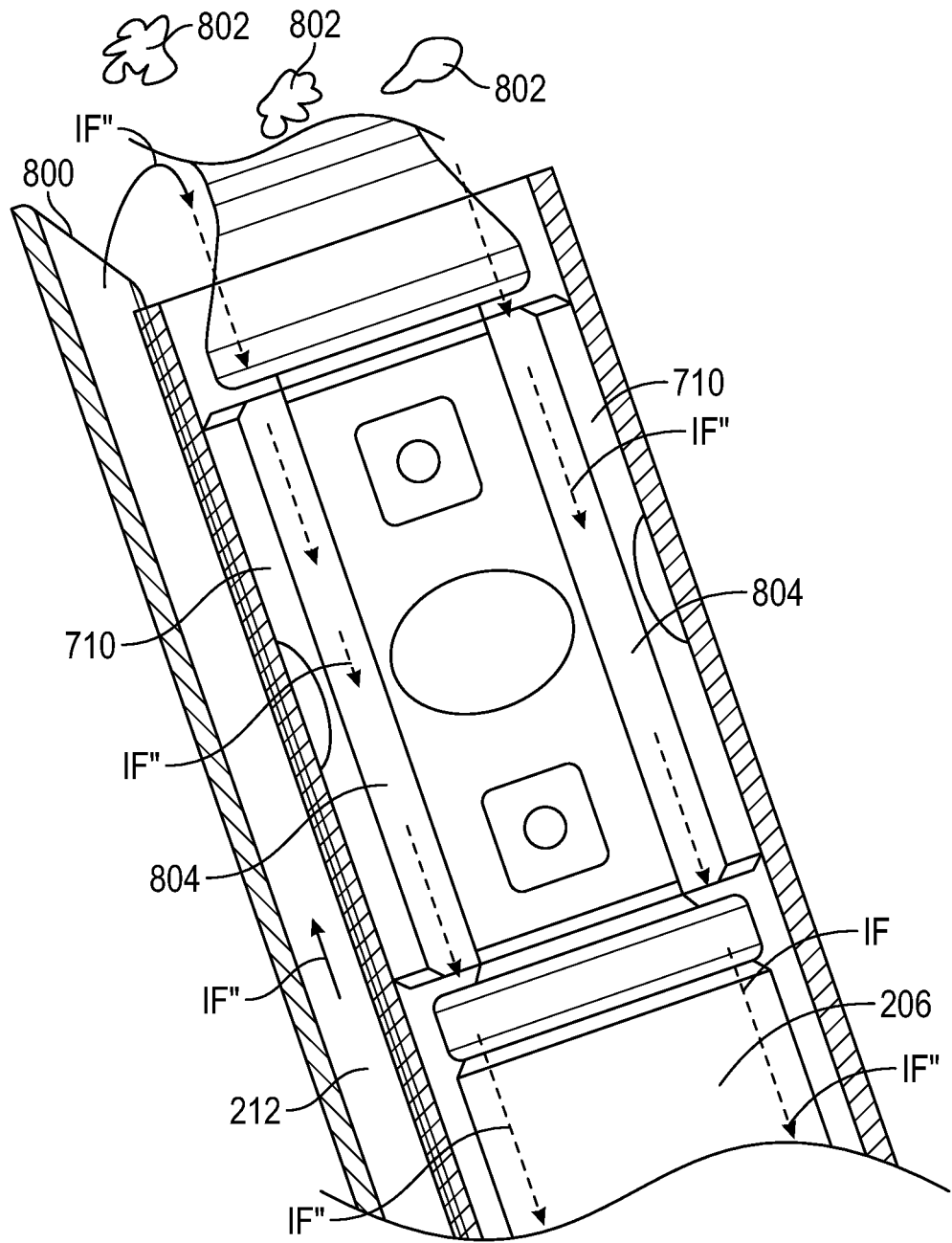

Making reference to FIG. 8, as noted above, the irrigation hypotube 212 can provide the irrigant portion IF" to the cutting implement 110. The irrigation hypotube 212 can include an outlet 800 through which the irrigant portion IF" can exit to the cutting implement 110. In an example, the cutting implement 110 can be cooled with the irrigant portion IF". Moreover, the irrigant portion IF" can remove debris 802 removed by the cutting implement 110 at a surgical site. As noted above, a suction can be applied at the orifices 314 and 316. In addition, the threaded configuration imparted by the helicoils 205 of the proximal coupler 204 can create vacuum pressure. In an example, the suction at the orifices 314 and 316 and the vacuum pressure operate to pull the irrigant portion IF" from the surgical site and the cutting implement 110 into ports 804 of the bearing 710. In an example, because of the suction at the orifices 314 and 316 and the vacuum pressure, the irrigant portion IF" can be pulled over the distal coupler 206 and into the port 400 (FIG. 4). Moreover, similar to the irrigant portion IF', the irrigant portion IF" flows towards the proximal coupler 204 as discussed above with reference to the irrigant portion IF'.

Figure 3:
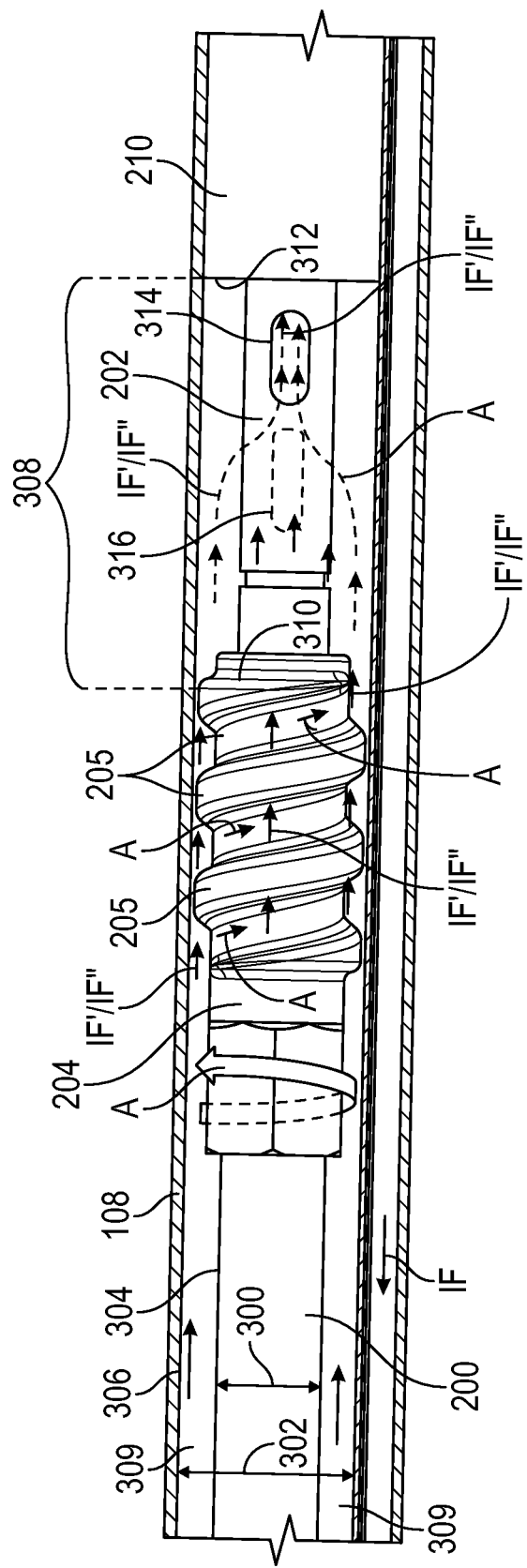
FIG. 3 illustrates a proximal coupler disposed within the outer tube of the handheld surgical instrument of FIG. 1, in accordance with at least one example of the present disclosure.

When the irrigant portion IF" arrives at the proximal coupler 204, the irrigant portion IF" can flow between the helicoils 205 as shown by the directional arrows A in FIG. 3. Furthermore, the irrigant portion IF" can travel over the helicoils 205, as shown with regards to FIG. 3. In an example, the irrigant portion IF" can travel past the proximal coupler 204 and into the irrigation outlet chamber 308. Moreover, due to the suction that can be applied to the orifices 314 and 316, similar to the irrigant portion IF', the irrigant portion IF" can be pulled from the proximal coupler 204 and into the orifices 314 and 316 for evacuation from the handheld surgical device 100.

As noted above, the handheld surgical device 100 includes the handpiece 102 and the irrigation hub interface 106. Now making reference to FIG. 9, a schematic view of the handpiece 102 and the irrigation hub 106 of FIG. 1 are shown, in accordance with an example. The handpiece 102 can include the motor 900 that can include cannulations 902 that can operatively couple the handpiece motor 900 with the proximal tube 202. In particular, the proximal tube 202 can include an interface 904 that can be configured to engage with the motor cannulations 902 such that the cannulations 902 rigidly hold the proximal tube 202 during rotation of the handpiece motor 900 and the proximal tube 202.

In an example, the proximal tube 202 can include an outlet 906 that can be in fluid communication with a suction outlet pathway 908. The suction outlet pathway 908 can be in fluid communication with a suction port 112 (FIG. 1). During operation of the handheld surgical device 100, a suction can be created that is fed through the suction outlet 112 and the suction outlet pathway 908. The proximal tube outlet 906 can be in fluid communication with the proximal tube orifices 314 and 316. Thus, the aforementioned suction applied at the proximal tube orifices 314 and 316 can be created from a suction source (not shown) that can be applied at the suction port 112. Moreover, in an example, the irrigant portions IF' and IF" can be pulled through the proximal tube 202, through the proximal tube outlet 906, into the suction outlet pathway 908, and then into the suction port 112.

In addition to puling the irrigant portions IF' and IF" out of the handheld surgical device 100, the handpiece 102 can be configured to provide the irrigant IF to the outer tube 108 and the irrigant pathway 218. More specifically, the handpiece 102 can include an irrigant supply line 910 coupled with an irrigant source 114 (FIG. 1). In an example, the handpiece 102 can be supplied with the irrigant IF via the irrigant source 114 where the irrigant IF travels through the handpiece 102 and into an irrigant outlet 912 aligned with the irrigant supply line 910. In an example, the irrigant outlet 912 can be disposed within the irrigation hub interface 106 and in fluid contact with the irrigant pathway 218. Thus, the irrigant IF can be provided to the irrigant pathway 218 from the handpiece 102 via the irrigant supply line 910 and the irrigant outlet 912.

Turning attention to the irrigation hub interface 106, the handpiece 102 can be fitted with different distal sections 104. Thus, different attachments may be affixed to the handpiece 102 depending on the intended use of the handheld surgical device 100. In an example, the irrigation hub interface 106 can be configured to removably engage with the handpiece 102. In particular, the irrigation hub interface 106 can be tapered such that the irrigation hub interface 106 can slidingly engage with the handpiece 102. For example, the irrigation hub interface 106 can include a first section 914 having a first width 916 along with a second section 918 having a second width 920 greater than the first width 916. In an example, the irrigation hub interface 106 can include tapered sections 922 where the irrigant outlet 912 can be disposed. In an example, the handpiece 102 can include tapers that compliment the tapered sections 922. Thus, in an example, the tapered sections 922 can have a flush fit within the handpiece 102.

Moreover, the first section 914 can include a dynamic seal 924 while the second section can include a dynamic seal 926. In an example, each of dynamic seals 924 and 926 can facilitate sealing engagement of the irrigation hub interface 106 within the handpiece 102. In an example, the dynamic seals 924 and 926 can be formed of any type of elastomeric polymers, rubber, or any other material that may provide a seal between the handpiece 102 and the irrigation hub interface 106. Moreover, in an example, the dynamic seals 924 and 926 can be o-rings. In an example, a backflow dynamic seal 925 can be configured to be disposed about the proximal tube 202 as shown with reference to FIG. 9. In an example, the backflow dynamic seal 925 can function to prevent the backflow of irrigant, such as the irrigant IF, the irrigant portion IF', and the irrigant portion IF" into the handpiece 102.

The handpiece 102 can also have a radio frequency (RF) housing 927 that includes a RF reader 928 configured to read RF tag (not shown) affixed to the irrigation hub interface 106. In an example, the RF tag can include information regarding a type of the cutting implement 110 and the settings to be used by an irrigation pump (not shown) to provide the irrigant IF. In addition, the RF tag can include information corresponding to the setting that can be used for a vacuum pump (not shown) coupled with the suction port 112 to ensure that a proper suction can be applied to allow for the irrigant portion IF' to flow into the cooling orifice 208 while at the same allowing the irrigant portion IF" to flow through the irrigation hypotube outlet 800. In an example, the cooling orifice 208 is located upstream of the irrigation hypotube outlet 800 relative to the irrigation hypotube outlet 800.

The handpiece 102 can also include a bearing 930 that can be configured to be disposed about the proximal tube interface 904 between the RF housing 927 and an inner hub 932. The bearing 930 can be configured to minimize axial forces from being transmitted to both the flexible shaft 200 and the proximal tube 202 during operation of the handheld surgical device 100. In particular, the bearing 930 can be configured to absorb axial forces that are translated to the inner hub 932 from the motor 900 during operation of the handheld surgical device 100.

Figure 10A:
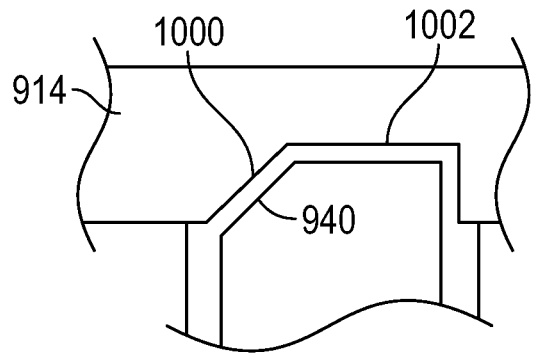
FIGS. 10A and 10B are schematics of a release of the handpiece in FIG. 9, in accordance with at least one example of the present disclosure.
Figure 10B:
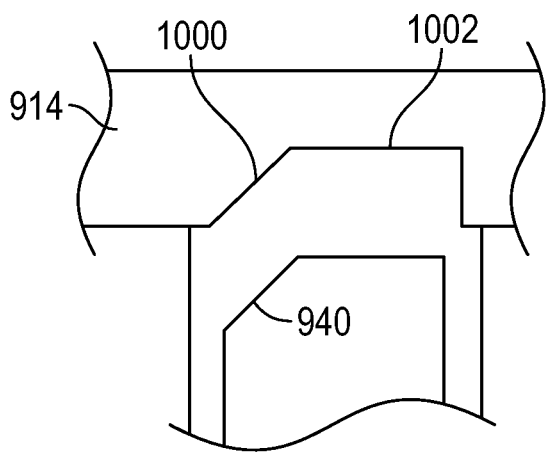
Figure 11:
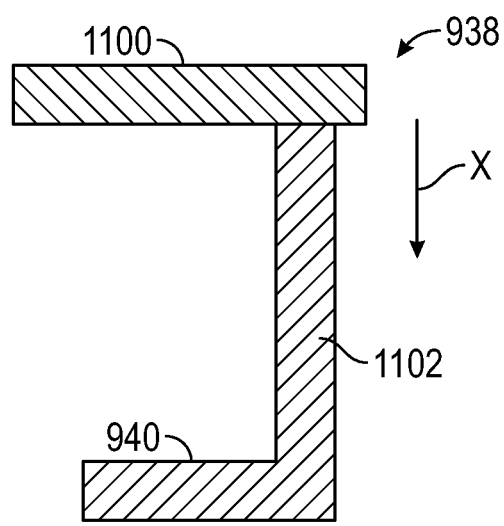
FIG. 11 shows a release of the handpiece in FIG. 9, in accordance with at least one example of the present disclosure.

In an example, the handpiece 102 can also include a release 938 having a lock that engages with a surface 1000 (FIG. 10A) of the first section 914. Making reference to FIG. 11, the release 938, which may be a button, or any other structure configurable to be engaged by a user, includes an engagement surface 1100 along with an arm 1102 coupled to both the engagement surface 1100 and the lock 940. When a user moves the engagement release 938 in a downward direction X, the lock 940 disengages with the surface 1000 of the first section 914 such that the lock 940 can be outside of a cavity 1002, as shown with reference to FIG. 10B. When the lock is outside of the cavity 1002, the distal section 104 and the irrigation hub interface 106 can be moved along a direction B (FIG. 9) such that the distal section 104 and the irrigation hub assembly 106 can be removed from the handpiece 102.

Having described various aspects and features of the inventive subject matter, the following numbered examples are provided as illustrative embodiments:

1. A disposable attachment comprising:
a distal section including:
an outer tube;
a flexible shaft disposed within the outer tube, the flexible shaft configured to couple with a proximal tube of a surgical instrument via a proximal coupler at a proximal end of the flexible shaft;
an irrigation hypotube disposed on an outer surface of the outer tube;
a cooling orifice disposed at the irrigation hypotube; and
a cutting implement disposed at a distal end of the distal section opposite the proximal coupler.

2. The disposable attachment of the handheld surgical instrument of example 1, wherein the outer tube has an inner diameter and the flexible shaft has an outer diameter that is less than the outer tube inner diameter such that a port is formed between the outer tube and the flexible shaft.

3. The disposable attachment of the handheld surgical instrument of examples 1 and 2, wherein the cooling orifice is disposed at a distal end of the irrigation hypotube and is configured to fluidly couple the irrigation hypotube with the port between the outer tube and the flexible shaft.

4. The disposable attachment of the handheld surgical instrument of examples 1-3, wherein the irrigation hypotube is configured to simultaneously provide irrigant to the cooling orifice and the cutting implement.

5. The disposable attachment of the handheld surgical instrument of examples 1-4, the distal section further comprising an irrigation hypotube outlet disposed at a distal end of the irrigation hypotube, the irrigation hypotube outlet sharing an irrigation source with cooling orifice where the cooling orifice is upstream of the irrigation hypotube outlet.

6. The disposable attachment of the handheld surgical instrument of examples 1-5, wherein the proximal tube is rotatable in a first direction along with the flexible shaft.

7. The disposable attachment of the handheld surgical instrument of examples 1-6, wherein the proximal coupler has a helical feature configuration and is configured to pull irrigant from the distal section during operation of the disposable attachment.

8. The disposable attachment of the handheld surgical instrument of examples 1-7, the proximal coupler further comprising:
a first cavity configured to receive the proximal end of the flexible shaft; and a second cavity opposite the first cavity, the second cavity configured to receive the proximal tube.

9. The disposable attachment of the handheld surgical instrument of examples 1-8, wherein an outer surface of the first cavity is crimped around the flexible shaft when the first cavity receives the flexible shaft proximal end.

10. The disposable attachment of the handheld surgical instrument of examples 1-9, wherein the disposable attachment attaches to the surgical instrument and the surgical instrument includes a bushing disposed about the proximal tube.

11. The disposable attachment of the handheld surgical instrument of examples 1-10, wherein the bushing and the proximal coupler define an irrigation outlet chamber about the proximal tube.

12. The disposable attachment of the handheld surgical instrument of examples 1-11, wherein a portion of the proximal tube in the irrigation outlet chamber includes a first orifice disposed between the proximal coupler and the bushing and a second orifice disposed between the proximal coupler and the bushing opposite the first orifice.

13. The disposable attachment of the handheld surgical instrument of example 1, wherein the disposable attachment of the handheld surgical instrument includes a bushing disposed about the proximal tube, the bushing including a first side opposite the proximal coupler and a second side opposite the first side, the irrigation hypotube including an irrigation port disposed near the second side of the bushing.

14. The disposable attachment of the handheld surgical instrument of example 1, the disposable attachment of the handheld surgical instrument further comprising a distal coupler disposed at the distal end of the distal section near the cutting implement, the distal coupler defining a first cavity configured to receive an end of the cutting implement and a second cavity opposite the first cavity, the distal coupler second cavity configured to receive a distal end of the flexible shaft opposite the proximal end of the flexible shaft, the cooling orifice being disposed adjacent the distal coupler.

15. The disposable attachment of examples 1-14, wherein the cutting implement is a burr.

16. The disposable attachment of examples 1-15, wherein the distal section includes a bendable portion located between the proximal coupler and the cooling orifice.

17. A disposable attachment comprising:
a distal section including:
an outer tube;
a flexible shaft disposed within the outer tube and configured to operatively couple with the proximal tube of a surgical instrument;
an irrigation hypotube disposed on an outer surface of the outer tube;
a cooling orifice disposed at the irrigation hypotube; and
a cutting implement disposed at a distal end of the distal section, wherein the outer tube has an inner diameter and the flexible shaft has an outer diameter that is less than the outer tube inner diameter such that a port is formed between the outer tube and the flexible shaft, the cooling orifice being configured to fluidly couple the irrigation hypotube with the port between the outer tube and the flexible shaft.

18. The disposable attachment of the handheld surgical instrument of example 17, wherein the irrigation hypotube has an outlet adjacent the cutting implement.

19. The disposable attachment of the handheld surgical instrument of examples 17 and 18, wherein the irrigation hypotube is configured to simultaneously provide first irrigant to the cooling orifice and second irrigant to the cutting implement.

20. The disposable attachment of the handheld surgical instrument of examples 17-19, wherein the port between the outer tube and the flexible shaft is configured to receive the first irrigant from the cutting implement and the second irrigant from the cooling orifice.

21. The disposable attachment of the handheld surgical instrument of examples 17-20, the irrigation hypotube further comprising an outlet disposed at the distal end of the irrigation hypotube, the irrigation hypotube outlet sharing an irrigation source with cooling orifice where the cooling orifice is upstream of the irrigation hypotube outlet.

22. The disposable attachment of the handheld surgical instrument of examples 17-21, wherein the irrigation hypotube is configured to simultaneously provide first irrigant to the cooling orifice and the irrigation hypotube outlet and second irrigant to the cutting implement.

23. The disposable attachment of the handheld surgical instrument of examples 17-22, the disposable attachment further comprising a distal coupler disposed at the distal end of the distal section, the distal coupler defining a first cavity configured to receive an end of the cutting implement and a second cavity opposite the first cavity, the distal coupler second cavity configured to receive a distal end of the flexible shaft opposite the proximal end of the flexible shaft, the cooling orifice being disposed adjacent the distal coupler.

24. The disposable attachment of examples 17-23, wherein the cutting implement is a burr.

25. A handheld surgical instrument, comprising:
a handpiece having:
a motor disposed within the handpiece;
a proximal tube operatively coupled with the motor such that the proximal tube is caused to rotate with the motor during operation of the handheld surgical instrument, the proximal tube extending from the disposable attachment
a distal section extending from the disposable attachment, the distal section including:
an outer tube;
a flexible shaft disposed within the outer tube, the flexible shaft coupling with the proximal tube via a proximal coupler at a proximal end of the flexible shaft, the proximal coupler comprising:
a first cavity configured to receive the proximal end of the flexible shaft; and
a second cavity opposite the first cavity, the second cavity configured to receive the proximal tube and operatively couple the proximal tube with the proximal coupler, the second cavity including an outer surface having a threaded configuration.

26. The disposable attachment of example 25, wherein the helical feature configuration is configured to pull irrigant from the distal section during operation of the handheld surgical instrument when the proximal tube is caused to rotate with the motor.

27. The disposable attachment of examples 25 and 26, wherein an outer surface of the first cavity is crimped around the flexible shaft when the first cavity receives the flexible shaft proximal end.

28. The disposable attachment of examples 25-27, wherein the disposable attachment includes a bushing disposed about the proximal tube.

29. The disposable attachment of examples 25-28, wherein the bushing and the proximal coupler define an irrigation outlet chamber about the proximal tube.

30. The disposable attachment of examples 25-29, wherein a portion of the proximal tube in the irrigant outlet chamber includes a first orifice disposed between the proximal coupler and the bushing and a second orifice disposed between the proximal coupler and the bushing opposite the first orifice.

31. The handheld surgical instrument of examples 25-30, the disposable attachment further comprising an irrigation hypotube disposed on an outer surface of the outer tube.

32. The handheld surgical instrument of examples 25-31, wherein the disposable attachment includes a bushing disposed about the proximal tube, the bushing including a first side opposite the proximal coupler and a second side opposite the first side, the irrigation hypotube including an irrigation port disposed near the second side of the bushing.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A disposable attachment comprising:
a distal section including:
an outer tube;
a flexible shaft disposed within the outer tube, the flexible shaft configured to couple with a proximal tube having an orifice via a proximal coupler at a proximal end of the flexible shaft, wherein the proximal tube is rotatable along with the flexible shaft and the proximal coupler has a helical feature configuration and is configured to pull irrigant from the distal section during operation of the disposable attachment, wherein the proximal coupler is configured to direct irrigant towards the proximal tube orifice via the helical feature;
an irrigation hypotube disposed on an outer surface of the outer tube;
a cooling orifice disposed at the irrigation hypotube;
a distal coupler disposed at a distal end of the distal section and coupled with the flexible shaft; and
a cutting implement coupled with the distal coupler.

2. The disposable attachment of claim 1, wherein the outer tube has an inner diameter and the flexible shaft has an outer diameter that is less than the outer tube inner diameter such that a port is formed between the outer tube and the flexible shaft.

3. The disposable attachment of claim 2, wherein the cooling orifice is configured to fluidly couple the irrigation hypotube with the port between the outer tube and the flexible shaft and the irrigation hypotube is configured to simultaneously provide irrigant to the cooling orifice and the cutting implement.

4. The disposable attachment of claim 2, the distal section further comprising an irrigation hypotube outlet disposed at a distal end of the irrigation hypotube, the irrigation hypotube outlet sharing an irrigation source with the cooling orifice where the cooling orifice is upstream of the irrigation hypotube outlet.

5. The disposable attachment of claim 1, wherein the proximal coupler further comprises:
a first cavity configured to receive the proximal end of the flexible shaft; and
a second cavity opposite the first cavity, the second cavity configured to receive the proximal tube.

6. The disposable attachment of claim 5, wherein an outer surface of the first cavity is crimped around the flexible shaft when the first cavity receives the flexible shaft proximal end.

7. The disposable attachment of claim 5, wherein the disposable attachment attaches to a surgical instrument and the surgical instrument includes a bushing disposed about the proximal tube and the bushing and the proximal coupler define an irrigation outlet chamber about the proximal tube and a portion of the proximal tube in the irrigation outlet chamber includes a first orifice disposed between the proximal coupler and the bushing and a second orifice disposed between the proximal coupler and the bushing opposite the first orifice.

8. The disposable attachment of claim 1, wherein the disposable attachment includes a bushing disposed about the proximal tube, the irrigation hypotube including an irrigation port disposed on a distal side of the bushing.

9. The disposable attachment of claim 1, wherein the distal coupler defines a first cavity configured to receive an end of the cutting implement and a second cavity opposite the first cavity, the distal coupler second cavity configured to receive a distal end of the flexible shaft opposite the proximal end of the flexible shaft, the cooling orifice being disposed adjacent the distal coupler.

10. The disposable attachment of claim 1, wherein the cutting implement is a burr.

11. The disposable attachment of claim 1, wherein the distal section includes a bendable portion located between the proximal coupler and the cooling orifice.

12. A disposable attachment comprising:
a distal section including:
an outer tube;
a flexible shaft disposed within the outer tube and configured to operatively couple with a proximal tube having an orifice via a proximal coupler at a proximal end of the flexible shaft, wherein the proximal tube is rotatable along with the flexible shaft and the proximal coupler has a helical feature configuration and is configured to pull irrigant from the distal section during operation of the disposable attachment, wherein the proximal coupler is configured to direct irrigant towards the proximal tube orifice via the helical feature;

an irrigation hypotube disposed on an outer surface of the outer tube;
a cooling orifice disposed at the irrigation hypotube;
a distal coupler disposed at a distal end of the distal section and coupled with the flexible shaft; and
a cutting implement coupled with the distal coupler, wherein the outer tube has an inner diameter and the flexible shaft has an outer diameter that is less than the outer tube inner diameter such that a port is formed between the outer tube and the flexible shaft, the cooling orifice being configured to fluidly couple the irrigation hypotube with the port between the outer tube and the flexible shaft.

13. The disposable attachment of claim 12, wherein the irrigation hypotube has an outlet adjacent the cutting implement and is configured to simultaneously provide first irrigant to the cooling orifice and second irrigant to the cutting implement and the port between the outer tube and the flexible shaft is configured to receive the first irrigant from the cutting implement and the second irrigant from the cooling orifice.

14. The disposable attachment of claim 12, the irrigation hypotube further comprising an outlet disposed at a distal end of the irrigation hypotube, the irrigation hypotube outlet sharing an irrigation source with the cooling orifice where the cooling orifice is upstream of the irrigation hypotube outlet and the irrigation hypotube is configured to simultaneously provide first irrigant to the cooling orifice and the irrigation hypotube outlet and second irrigant to the cutting implement.

15. The disposable attachment of claim 12, wherein the distal coupler defines a first cavity configured to receive an end of the cutting implement and a second cavity opposite the first cavity, the distal coupler second cavity configured to receive a distal end of the flexible shaft opposite the proximal end of the flexible shaft, the cooling orifice being disposed adjacent the distal coupler.

16. The disposable attachment of claim 12, wherein the cutting implement is a burr.

17. A handheld surgical instrument, comprising:
a handpiece having:
a motor disposed within the handpiece;
a disposable attachment having a proximal tube operatively coupled with the motor such that the proximal tube is caused to rotate with the motor during operation of the handheld surgical instrument, wherein the proximal tube
has an orifice; and
extends from the handpiece;
a distal section extending from the handpiece, the distal section including:
an outer tube;
a flexible shaft disposed within the outer tube, the flexible shaft coupling with the proximal tube via a proximal coupler at a proximal end of the flexible shaft, wherein the proximal tube is rotatable along with the flexible shaft, the proximal coupler comprising:
a helical feature configuration that is configured to pull irrigant from the distal section during operation of the disposable attachment, wherein the proximal coupler is configured to direct irrigant towards the proximal tube orifice via the helical feature;
a first cavity configured to receive the proximal end of the flexible shaft; and
a second cavity opposite the first cavity, the second cavity configured to receive the proximal tube and operatively couple the proximal tube with the proximal coupler, the second cavity including an outer surface having a threaded configuration.

18. The disposable attachment of claim 17, wherein the helical feature configuration is configured to pull the irrigant from the distal section during operation of the handheld surgical instrument when the proximal tube is caused to rotate with the motor, the disposable attachment of the handheld surgical instrument further comprising an irrigation hypotube disposed on an outer surface of the outer tube, wherein the disposable attachment of the handheld surgical instrument includes a bushing disposed about the proximal tube, the irrigation hypotube including an irrigation port disposed on a distal side of the bushing.

19. The disposable attachment of the handheld surgical instrument of claim 17, wherein an outer surface of the first cavity is crimped around the flexible shaft when the first cavity receives the flexible shaft proximal end.

20. The disposable attachment of the handheld surgical instrument of claim 17, wherein the handheld surgical instrument includes a bushing disposed about the proximal tube and the bushing and the proximal coupler define an irrigation outlet chamber about the proximal tube, wherein a portion of the proximal tube in the irrigant outlet chamber includes a first orifice disposed between the proximal coupler and the bushing and a second orifice disposed between the proximal coupler and the bushing opposite the first orifice.

* * * * *